United States Patent [19]

Hepburn

[11] Patent Number: 4,944,290
[45] Date of Patent: Jul. 31, 1990

[54] ADJUSTABLE SPLINT

[75] Inventor: George R. Hepburn, Severna Park, Md.

[73] Assignee: Dynasplint Systems, Inc., Baltimore, Md.

[21] Appl. No.: 229,967

[22] Filed: Aug. 9, 1988

[51] Int. Cl.⁵ .............................................. A61F 5/00
[52] U.S. Cl. ................................. 128/87 R; 128/87 A; 128/88; 128/77
[58] Field of Search .................. 128/87 R, 87 A, 87 B, 128/80 F, 88, 77, 878, 879

[56] References Cited

U.S. PATENT DOCUMENTS

| | | | |
|---|---|---|---|
| 1,366,576 | 1/1921 | Maddox | 128/87 R |
| 2,237,252 | 4/1941 | Longfellow | 128/87 R |
| 2,646,794 | 7/1983 | Baer | 128/87 A |
| 3,330,270 | 7/1967 | Brown | 128/87 R |
| 3,719,187 | 3/1973 | Ulansey | 128/87 R |
| 4,254,766 | 3/1981 | Kordis | 128/87 R |
| 4,456,002 | 6/1984 | Barber | 128/87 A |
| 4,485,808 | 12/1984 | Hepburn | 128/87 R |
| 4,508,111 | 4/1985 | Hepburn | 128/87 R |
| 4,538,600 | 9/1985 | Hepburn | 128/88 |
| 4,657,000 | 4/1987 | Hepburn | 128/87 R |
| 4,665,905 | 5/1987 | Brown | 128/87 R |
| 4,813,406 | 3/1989 | Ogle, III | 128/87 R |

FOREIGN PATENT DOCUMENTS

| | | | |
|---|---|---|---|
| 0176320 | 8/1961 | Sweden | 128/87 R |
| 0929317 | 6/1963 | United Kingdom | 128/87 A |

Primary Examiner—Robert A. Hafer
Assistant Examiner—Michael Brown
Attorney, Agent, or Firm—Larson and Taylor

[57] ABSTRACT

An ajustable splint assembly is shown. The assembly is composed of a distal strut and a proximal strut pivotably connected to the distal strut. One of the struts has at one end a pivotably mounted head portion defining a cam surface. The other strut has an adjustable biasing means mounted within it and is biased into engagement with the cam surface for applying a quantifiable force tending to align or proximate said upper and lower struts. A limb cradle is slidably mounted on the distal strut. The splint assembly also includes means for laterally adjusting said cradle to accommodate a limb part, a platform for supporting a proximal limb part, means connecting said platform to the proximal strut, said platform being longitudinally adjustable, and means for securing said splint assembly to the limb.

6 Claims, 3 Drawing Sheets

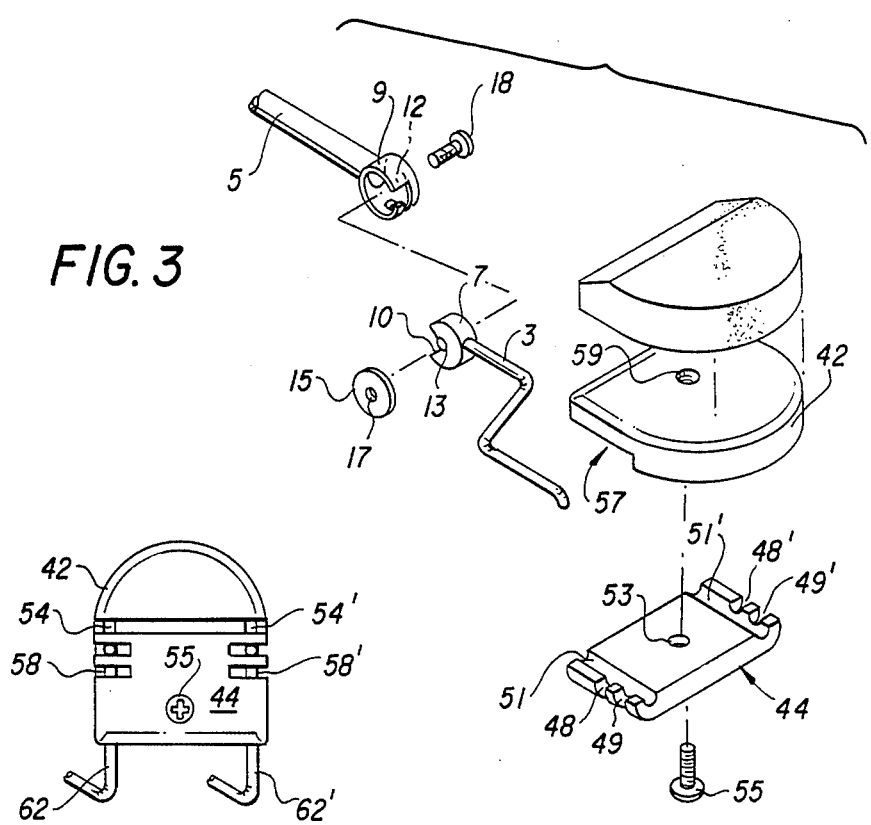
FIG. 3
FIG. 5
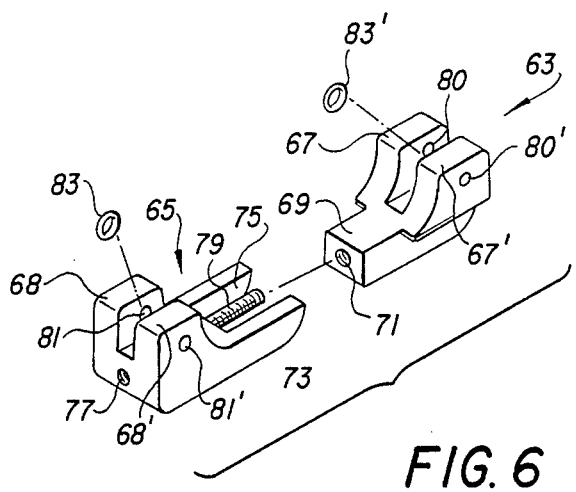
FIG. 6

ADJUSTABLE SPLINT

BACKGROUND OF THE INVENTION

1. Field of the Invention

This invention relates to an adjustable splint. More particularly, this invention relates to an adjustable splint useful in treating impairments in body joints and the like from flexion or extension contractures, weakness in the supporting musculature, or some other malady inhibiting the integrity of the body joint in accomplishing flexion or extension.

People often develop flexion and extension contractures in body joints such as finger joints from many and various causes. Weakness, disuse, fractures, surgeries, traumatic injuries, illness and other causes have been known to cause loss of ability to extend or flex the body joint. No device presently exists to reduce flexion contractures of finger joints by adjustable, quantifiable pressure as does the adjustable splint described herein.

Many splint devices and mechanisms have been designed to be influential at the knee, elbow or wrist, either for support or for mobilizing the joints. Illustrative of such devices are those described in U.S. Pat. Nos. 3,055,359; 3,785,372; 3,799,159; 3,928,872; 4,397,308; 4,485,808; 4,508,111; 4,538,600; and 4,657,000. However, all of these devices are not designed to reduce finger joint flexion or extension contractures and cannot be tolerated by the patient population for a long enough period to effectively reduce a contracture.

OBJECTIONS OF THE INVENTION

Accordingly, it is an object of the invention to provide an improved splint device for reducing flexion and extension contractures about a body joint, particularly a digit (i.e., finger and toe) joint.

Yet another object of the invention is to provide a splint device, which allows easy gradual adjustment to the quantifiable force desired on an extremity acting across a body joint.

A further object of the invention is to provide a splint device for resolving stiffness or contracture that has resulted from illness, surgery or joint trauma including but not limited to arthrotomies, ligamentous repairs, arterial and venous microsurgical repair, rheumatoid arthritis, hemophilia, fractures and burns.

A further object would be to provide an improved splint for providing support to a limb around a body joint such as a knee, elbow, wrist, finger or toe.

SUMMARY OF THE INVENTION

These and other objects of the invention are obtained by an adjustable splint assembly comprising a distal strut and a proximal strut pivotably connected to said distal strut, one of said struts having at one end a pivotably mounted head portion defining a cam surface, an adjustable biasing means mounted within the other strut and biased into engagement with said cam surface, for applying a quantifiable force tending to approximate or align said upper and lower struts, a limb cradle slidably mounted on the distal strut, means for laterally adjusting said cradle to accommodate a limb part, a platform for supporting a proximal limb part, means connecting said platform to the proximal strut, said platform being longitudinally adjustable, and means for securing said splint assembly to the limb.

(The term "limb" as used herein and in the appended claims is meant a leg, arm, hand, finger or toe.)

In a preferred embodiment, the present invention comprises a pair of distal struts and a pair of proximal struts, each member of the pair of distal struts being pivotably connected to a member of the proximal struts, said members of each pair being spaced apart a distance to accomodate limb parts distal and proximal to the limb joint, at least one of said struts having at one end a pivotably mounted head portion defining a cam surface, an adjustable biasing means mounted within the strut pivotably connected to said cam surface-containing strut and biased into engagement with said cam surface, for applying a quantifiable force tending to align or approximate the cam surface-containing strut with the adjustable biasing means containing strut, a limb cradle slidably mounted on said pair of distal struts, means for laterally adjusting said cradle to accomodate a limb part, a platform for supporting a proximal limb part, separate means connecting said platform to the pair of proximal struts, said platform being longitudinally adjustable, and means provided at least said pair of proximal struts for securely holding therebetween proximal parts of a limb.

The limb cradle of the invention is preferably comprised of a first part and a second part, said first part comprising a base section and a side section provided with an opening through which it is slidably mounted to one of the pair of distal struts, said second part comprising a side section provided with an opening through which it is slidably mounted to the other of the pair of distal struts and a base section having a slot for receiving the base section of said first part to thereby join said first and second parts so as to form a cradle and means for securing and laterally adjusting said first and second parts.

In a preferred embodiment, the platform for supporting a proximal limb part and the means for longitudinally adjusting same comprise a top plate, a base plate, means for capturing the end portion of each means connecting the platform to the proximal strut or struts and means for securing the baseplate to the top plate.

Advantageously, a pair of proximal struts and a pair of distal struts are employed in which case the ends of the distal struts are connected to the platform by a pair of spaced apart connecting means, the proximal end portions of which are mounted in the platform.

BRIEF DESCRIPTION OF THE DRAWINGS

The invention will appear more clearly from the following detailed description when taken in connection with the following drawings which show by way of example a preferred embodiment of the invention:

In the Drawings:

FIG. 3 is a perspective, exploded view in part of one distal and one proximal strut assembly together with an exploded view of the platform.

FIG. 5 is a rear perspective view of the platform attached to a pair of the means connecting same to the distal struts.

FIG. 6 is an exploded perspective view of the cradle before mounting on the pair of distal struts.

DESCRIPTION OF THE PREFERRED EMBODIMENTS

Figure 1:
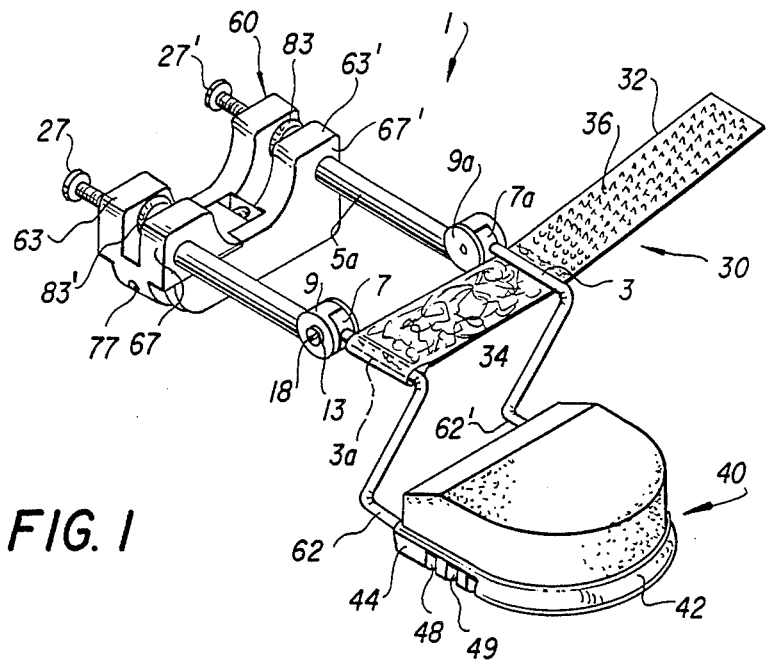
FIG. 1 is a perspective view of the adjustable splint for reducing flexion contractures.
Figure 2:
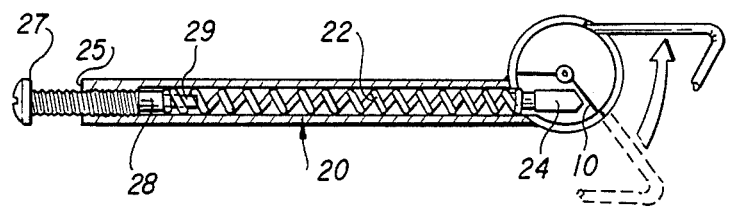
FIG. 2 is a perspective view of one distal and one proximal strut assembly of the adjustable splint of the invention for reducing flexion contractures wherein a strut is broken away to show the adjustable spring-loaded means mounted therein.

Referring to FIGS. 1-3, an adjustable splint device 1 is comprised of proximal struts 3 and 3a and distal struts 5 and 5a. Proximal strut 3 contains a rounded head portion 7 and distal strut 5 contains a socket head portion 9 having a screw hole 12 which receives head portion 7 for pivotable engagement therewith. Rounded head portion 7 is cut away to define a cam surface 10 and is provided with an axial screw hole 13. A surface plate 15 having an axially threaded screw hole 17 covers one side of the combined head portions 7-9. When surface plate member 15 is positioned over the combined head portion 7-9, a screw member 18 passes through the axial screw holes 12 and 13 and threads into screw hole 17. Proximal strut 3a and distal strut 5a are similarly pivotably connected by corresponding members bearing like numbers but carrying the distinguishing suffix "a".

The proximal and distal struts may be constructed of any material of sufficient strength such as plastic, metal, wood and the like. Particularly preferred are struts made of stainless steel metal. At least one of the struts should be at least partially hollow so as to house therein the adjustable spring mechanism of the invention. As shown in the drawings, the distal struts are tubular in construction and the proximal struts are solid. If desired, however, all of the struts can be tubular in construction so as to provide a lightweight product. Also if desired, each of the struts 3, 3a, 5 and 5a can be comprised of two telescoping portions so as to permit lengthening and shortening of the struts.

The adjustable spring-loaded mechanism designated generally as 20 may be provided in either the proximal or the distal struts. Preferably, however, it is the distal struts 5 and 5a that are provided with the adjustable spring mechanism.

Figure 4:
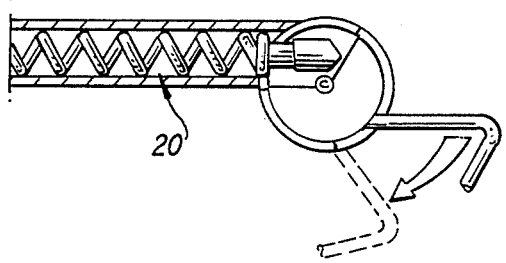
FIG. 4 is a perspective view of one distal and one proximal strut assembly of the adjustable splint of the invention for reducing extension contractures wherein a strut is broken away to show the adjustable spring-loaded means mounted therein.

The adjustable spring mechanism 20 is comprised of a spring 22 to which is attached a nose element 24 that bears on cam surface 10. Coil or clock springs are generally preferred but in some instances leaf springs are advantageously employed. An adjustable screw means indicated generally as 25 abuts the other end of the spring 22 and produces a quantifiable force which tends to either extend (i.e., align the proximal strut 5 with the distal strut 3 and proximal strut 5a with distal strut 3a in a parallel fashion) as shown in FIG. 2 or to approximate (i.e., bring together the proximal strut 5 with the distal strut 3 and proximal strut 5a with distal strut 3a) as shown in FIG. 4. As maximum flexion is approached, tension is created in the compression coiled spring 22. The adjustable screw means 25 is comprised of a slotted head screw 27, spring spacer 29 and loading nut 28. The head screw 27 is screwed into threaded end 30 with a conventional screwdriver blade until it abuts loading nut 28. Continued turning of the screw will cause loading nut 28 to abut spring spacer 29 which in turn abuts spring 22. The turning of the screw creates greater compression of spring 22 thereby exerting greater force on the cam surface 10 of the proximal strut 5 to exert a one way tension. The tension capability of the spring mechanism can range from 0 pounds tension up to the maximum tension capable of the spring. In general, the tension of the spring mechanism will range from 0 pounds up to 5 pounds of tension and the tension exerted by the spring can be varied at any point of joint range of motion, say from 20° flexion to 70° extension of the joint.

Whereas the specific joint range of motion to which tension can be exerted is preferred to be 65° flexion through +25° extension for reducing flexion contractures in the finger, the joint range of motion at which tension can be applied can vary to nearly any degree in the 360° circular range simply by varying the point of attachment of the inner portion of strut 3 to rounded head portion 7 and by varying the point of attached of the inner portion of strut 5 to socket head portion 9. Likewise, the same variations apply to struts 3a and 5a.

The purpose of varying the point in the joint range to which tension is applied is obvious when you consider that different illnesses and injuries cause different types of limitations at different degrees of joint ranges of motion thereby making necessary different points in the joint range at which tension must be applied to improve their condition. The spring mechanism can be calibrated to exert the desired range of tension. The calibration can be effected by determining the kilogram-centimeter torque provided at a tension screw setting, e.g., the distance the screw 27 projects from the end of the distal strut 5 and/or strut 5a. Alternatively, the calibration can be effected by providing load nut 27 with a poundage indicator line and a calibration scale 37 (not shown) about the proximal strut 5 which scale can be provided with a slot (not shown) through which the poundage indicator (not shown) is visible.

While the preferred adjustable biasing means of the invention is a spring means such as described, equivalent biasing means such as air or hydraulic powered biasing means will readily come to the mind of those skilled in this art.

Any suitable means can be utilized to secure pivotably mounted struts 3 and 5 and pivotably mounted struts 3a and 5a to the limb so that they lie lateral to the joint with the axis of rotation coinciding as closely as possible to the axis of rotation of the joint. As shown in the figures, the securing means comprise a proximal cuff 30 attached at one end to a proximal strut. The other end of the cuff extends under and around the other proximal strut. The length of the proximal cuff 30 is of sufficient distance to comfortably accomodate the limb parts proximal to the limb joint. An overlying section 32 of the cuff 30, attached to strut 3 contains on its outer surface an attaching means such as velcro hooks 34 by which the flap can wrap about the proximal portion of the limb and be secured to velcro loops 36 on the outer surface of the proximal cuff wrapped about upper strut 3. When wrapped around the limb and secured, the cuff serves as a counterforce strap. If necessary, distal struts 5 and 5a can be provided with a similar cuff.

It should be understood that a single combined strut, such as strut 3 pivotably connected to strut 5 can alone be utilized as a splint device by securing same by suitable means to the lateral side of the limb to be treated. Again, any suitable means for strapping or securing the splint device of the invention can be used, for example, by distal and proximal cuffs of sufficient lengths to wrap around the distal and proximal portions of the limb being treated. The straps and/or cuffs can be secured to the struts in any suitable manner as by sewing, tying, etc.

The platform designated generally as 40 is comprised of a top plate 42 and a base plate 44. A pad 46 of foam plastic or rubber rests on top plate 42. Referring to FIG. 3 and FIG. 5, it is seen that one side of base plate 44 is provided with spaced, perpendicular slots 48 and 49 and the other side with counterpart slots 48' and 49'. A groove 51 is provided on the surface of base plate 44 and extends from the distal end of the base plate across the slots 48 and 49. On other other side of base plate 44 a groove 51' extends across slots 48' and 49' in a similar fashion. A hole 53 traverses base plate 44 and receives a screw 55.

Figure 7:
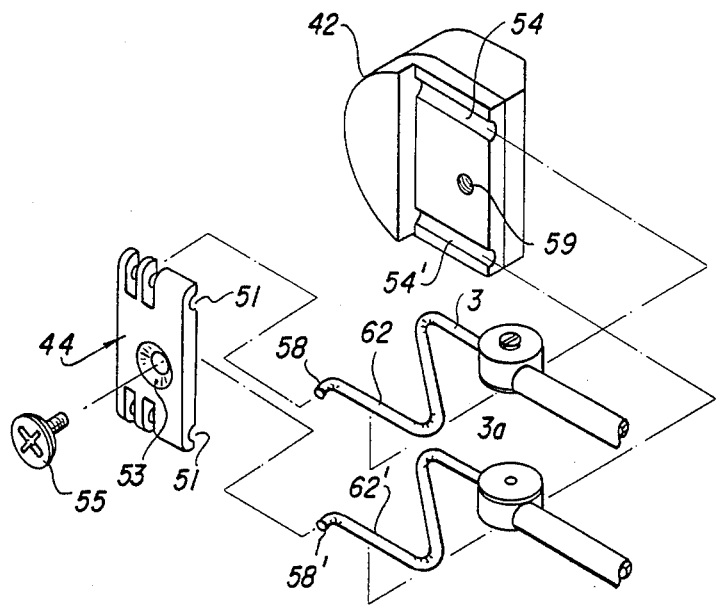
FIG. 7 is an exploded perspective view of the platform and means connecting same to the distal struts.
Figure 8:
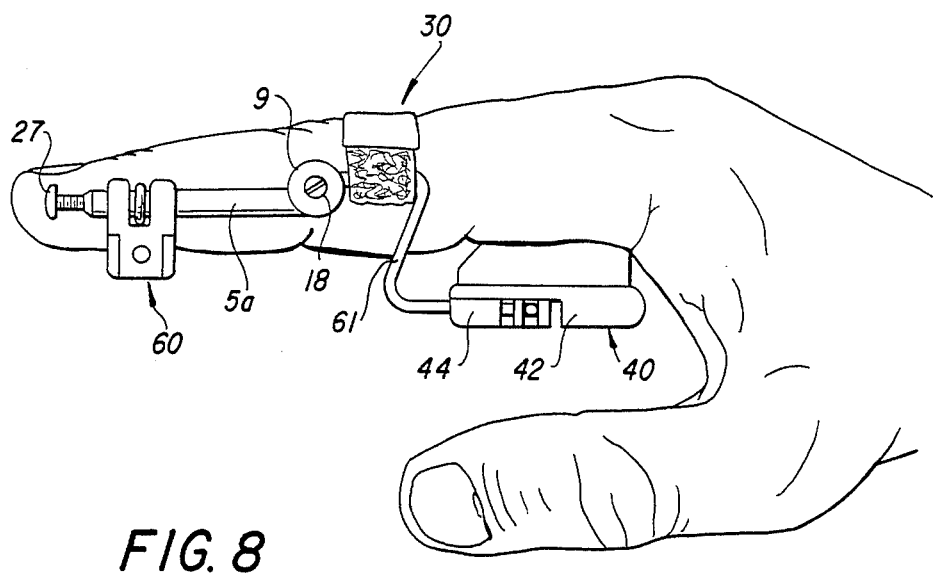
FIG. 8 is a perspective view of the splint assembly in use on a proximal interphalangeal joint.

Referring to FIGS. 5 and 7, top plate 42 contains a recessed portion designated generally as 57 shaped and dimensioned so as to accomodate base plate 44. On each side of the bottom surface of top plate 42 there are provided grooves 54 and 54'. A hole 59 is provided in top plate 42 at a location which aligns it with hole 53 of the base plate 44 when the top plate and base plate are joined together with a screw 55. Also, when base plate 44 is fitted into the recessed portion 57 of the top plate 42 and secured thereto, the respective grooves 51, 54 and 51' and 54' combine to form channels that receive and capture hook-shaped ends 58 and 58' of angle wires 62 and 62', respectively, by which platform 40 is connected to proximal struts 3 and 3a. In the embodiment illustrated, the proximal struts 3 and 3a are wires integral with connecting wires 62 and 62'. It should be understood, however, that the proximal struts can taken on a different form such as tubular structure and that the connecting means can be any convenient means for attaching the platform that allows for longitudinal adjustment of the platform. Hooked-shaped ends 58 and 58' of wires 62 and 62', respectively, hook into the slots 48, 49 or 50 and 48', 49' and 50', respectively, when the wires are positioned in the channels formed by the grooves 51, 51', 54 and 54'.

Referring to FIG. 6, the cradle 60 of the splint assembly is composed of two separate parts, a first part 63 and a second part 65. First part 63 has a pair of upwardly projecting side sections 67 and 67' and a tongue-shaped base section 69 provided at each end with a threaded screw hole 71. Second part 65 also comprises a pair of upwardly projecting side sections 68 and 68' and a base section 73 having a slot 75 that receives tongue-shaped base section 69 of first part 63. A hole 77 passing through the end of side section 67' of the second part and opening into slot 75 is provided with a captured screw 79, the end of which is threaded into hole 71 of tongue-shaped base section 69. Parts 63 and 65 are joined by inserting tongue-shaped base section 69 into space 75 and screwing captured screw 79 into threaded hole 71 of part 69. Thus, cradle 66 can be laterally adjusted to accomodate the width of a limb by simply screwing and unscrewing captured screw 79.

Spaced apart upper sections 67 and 67' are provided with holes 80 and 80' therethrough in longitudinal alignment with each other so that distal strut 5a can be slidably mounted therein. Similarly, upper sections 68 and 68' contains holes 81 and 81' therethrough in alignment with each other so that distal strut 5 can be slidably mounted therein. Advantageously, O-rings 83 and 83' are positioned within the spaced side section 67 prior to mounting of struts 5 and 5a. Once mounted, the cradle 60 is longitudinally adjusted by simply sliding the cradle 60 distally or proximally the desired distance.

With reference to FIG. 7, operation of the splint assembly of the invention will now be described in connection with the treatment of a flexion contracture of a proximal interphalangeal joint.

With tension screws 27 and 27' back out 8 mm, the finger to be treated is slipped into the splint assembly so that the joints of the splint are in line with the finger's proximal interphalangeal joint. If needed, the position of the platform 44 is adjusted so that it rests on the volar surface of the metacarpal head 90. The finger cradle 60 is then adjusted screwing or unscrewing captured screw 79 to achieve a comfortable width for both the cradle and the inner joint. If the finger is swollen at the proximal interphalangeal joint, widening the finger cradle will open the space between the splint joints and the patient's proximal interphalangeal joint. The finger cradle is then longitudinally adjusted by finger pressure to slide the cradle as close as possible to, but not beyond, the distal interphalangeal joint. Lastly, the counterforce strap 30 is then adjusted to maintain placement of the splint assembly in line with the patient's proximal interphalangeal joint axis of rotation.

The unique characteristics of the adjustable spring-loaded mechanism of the present invention is that it allows for adjustment of quantifiable force on an extremity acting across the body joint from 0 foot poundage up to maximum foot poundage at various body joint ranges.

As an example, in a patient having a finger flexion contracture, one may want to apply the splint to the finger and building in a tension of 0.1 foot pound of force acting on the finger at finger extension. As the patient develops greater tolerance to the device, in days to come, greater force can be adjusted in the mechanism by simply tightening the tension screws 27 and 27' to cause greater compression to the spring in the strut thereby exerting a greater force toward extending the joint which will ultimately serve a more beneficial purpose in accomplishing reduction of the finger flexion contracture. In addition, the invention permits the interchangability of springs bearing force-exerting capabilities so as to allow for varying the degrees of tension exerted by the spring mechanism depending upon the particular use to which the device is applied.

The platform and the means for adjusting same insures proper location of same so as to achieve the optional combination of patient comfort and mechanical leverage.

Once the beginning tension and duration of splint application is determined, progression of the tension and duration can be accomplished by simple adjustment of the tension screws 27 and 27' and increasing time, respectively.

A unique feature of this device in the present application to the fingers, and to any body joint, is the ability of this device to allow graduated, quantified, adjustable tension with the ability to relax the stretch across the joint by flexing the finger from the limitation of extension. This will allow the tissue being stretched to have a rest period while not disturbing the adjustment of the spring tension and without having to remove the splint. In order to relieve the pressure on the contractured tissues, one merely has to overcome, by any means, the tension in the splint and flex the joint to a comfortable posture. Once a short rest is achieved, the splint may again exert its tension against the contractured tissue to help accomplish a greater degree of extension in the joint.

While the features of this invention have been disclosed with reference to the specific embodiments described therein, it is to be understood that various modifications may be made in the construction without departing from the scope of the invention as defined in the appended claims.

It is claimed:

1. An adjustable splint assembly comprising a distal strut and a proximal strut pivotably connected to said distal strut, one of said struts having at one end a pivotably mounted head portion defining a cam surface, an adjustable biasing means mounted within the other strut and biased into engagement with said cam surface, for applying a quantifiable force tending to proximate or align said upper and lower struts, a limb cradle slidably mounted on the distal strut and defining an area in which a limb is received, means for adjusting said cradle to vary the size of said area so as to accomodate a limb part of different size, a platform for supporting a proximal limb part, means connecting said platform to the proximal strut, said platform being longitudinally adjustable, and means for securing said splint assembly to the limb.

2. An adjustable splint assembly according to claim 1 wherein the adjustable biasing means is an adjustable spring means.

3. An adjustable splint assembly according to claim 1 wherein the adjustable spring means comprises a spring, a nose element connected to one of said spring, an adjustable screw means engageable with the other end of said spring.

4. An adjustable splint assembly according to claim 1 wherein the strut in which the adjustable spring mean is mounted is hollow.

5. An adjustable splint assembly according to claim 1 wherein the limb cradle is comprised of a first part and a second part, said first part comprising a base section and a pair of spaced side sections provided with an opening through which said second part is slidably mounted to one of the pair of distal struts, said second part comprising a pair of spaced side sections provided with an opening through which said second part is slidably mounted to the other of the pair of distal struts and a base section having a slot for receiving the base section of said first part to thereby join the first and second parts so as to form a cradle, and means for securing and laterally adjusting said first and second parts.

6. An adjustable splint assembly according to claim 1 wherein the platform and the means for a longitudinally adjusting said platform comprises a top plate, a base plate, means for capturing the end portion of said means connecting the platform to the proximal strut or struts and means for securing the base plate to the top plate.

* * * * *